(12) United States Patent
Bennett et al.

(10) Patent No.: US 9,987,169 B2
(45) Date of Patent: Jun. 5, 2018

(54) THREE-DIMENSIONAL ATTACHMENT APPARATUS FOR HEARING PROTECTION DEVICES

(71) Applicant: Otogear, Inc., Vancouver, WA (US)

(72) Inventors: Madeline Bennett, Seattle, WA (US); Maria Merakov, Bellevue, WA (US)

(73) Assignee: Otogear, Inc., Vancouver, WA (US)

( * ) Notice: Subject to any disclaimer, the term of this patent is extended or adjusted under 35 U.S.C. 154(b) by 0 days. days.

(21) Appl. No.: 15/140,143

(22) Filed: Apr. 27, 2016

(65) Prior Publication Data

US 2016/0310326 A1 Oct. 27, 2016

Related U.S. Application Data

(60) Provisional application No. 62/153,413, filed on Apr. 27, 2015.

(51) Int. Cl.
| | |
|---|---|
| *A61F 11/08* | (2006.01) |
| *H05B 33/08* | (2006.01) |
| *H05B 37/02* | (2006.01) |

(52) U.S. Cl.
CPC .......... *A61F 11/08* (2013.01); *H05B 33/0842* (2013.01); *H05B 37/0236* (2013.01); *H05B 37/0272* (2013.01); *Y02B 20/341* (2013.01)

(58) Field of Classification Search
CPC . A61F 11/08; H05B 33/0842; H05B 37/0236; H05B 37/0272; Y02B 20/341
See application file for complete search history.

(56) References Cited

U.S. PATENT DOCUMENTS

| | | | | |
|---|---|---|---|---|
| 4,582,053 | A  * | 4/1986 | Wilson | A61F 11/08 |
| | | | | 128/867 |
| 6,448,819 | B2 * | 9/2002 | Lin | H01R 33/09 |
| | | | | 362/658 |
| D585,053 | S  * | 1/2009 | Zeiss | D14/223 |
| D589,933 | S  * | 4/2009 | Zeiss | D14/205 |
| D590,055 | S  * | 4/2009 | Butler | D24/106 |
| D595,838 | S  * | 7/2009 | Butler | D24/106 |
| D601,691 | S  * | 10/2009 | Butler | D24/106 |
| D601,693 | S  * | 10/2009 | Butler | D17/14 |
| 8,570,170 | B2 * | 10/2013 | Zhang | H04M 1/72569 |
| | | | | 340/540 |

(Continued)

*Primary Examiner* — Sonia Gay
(74) *Attorney, Agent, or Firm* — George C. Rondeau, Jr.; Davis Wright Tremaine LLP

(57) ABSTRACT

An ornamental attachment apparatus is provided for attaching to and ornamenting hearing protection devices. The ornamental attachment apparatus includes an ornamental portion having ornamental feature, and a receiving portion for receiving and attaching to a post portion of a hearing protection device. The receiving portion may include a cavity including an attachment element for retaining the post portion therein. In some embodiments, the ornamental attachment apparatus includes an attachment element with a tapered shape for insertion into a recess on a custom hearing protection device. The ornamental portion may include a sensor, a peripheral device and an electronic component for controlling the peripheral device. The electronic component may be configured to control the peripheral device responsive to an electronic signal received from the sensor.

34 Claims, 10 Drawing Sheets

(56) References Cited

U.S. PATENT DOCUMENTS

| | | | |
|---|---|---|---|
| 2002/0090104 A1* | 7/2002 | Ma | H04R 1/1091 381/374 |
| 2007/0047740 A1* | 3/2007 | Andrea | H04R 1/1041 381/74 |
| 2007/0291974 A1* | 12/2007 | Eisenbraun | H04R 1/1016 381/370 |
| 2009/0034774 A1* | 2/2009 | Lowry, Jr. | H04R 1/1091 381/380 |
| 2011/0294350 A1* | 12/2011 | Stagi | H01R 4/20 439/623 |
| 2013/0103002 A1* | 4/2013 | Fruenlund | A61M 39/10 604/533 |
| 2013/0287241 A1* | 10/2013 | Prelogar | H04R 1/105 381/381 |
| 2014/0190493 A1* | 7/2014 | Smith | A61F 11/08 128/867 |
| 2015/0304762 A1* | 10/2015 | Schwartz | H04R 1/1091 381/380 |

\* cited by examiner

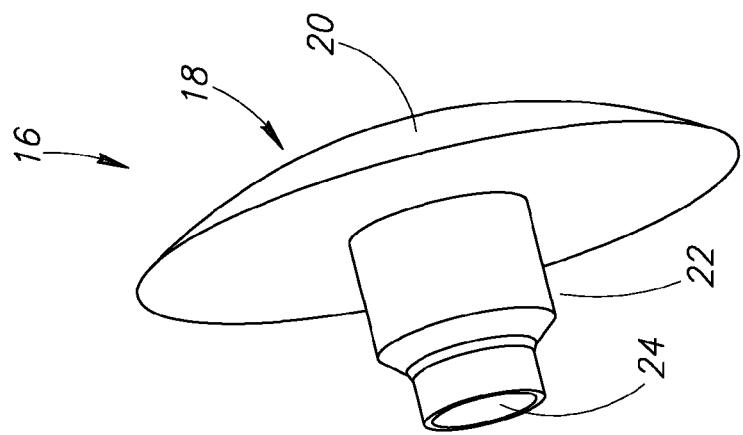
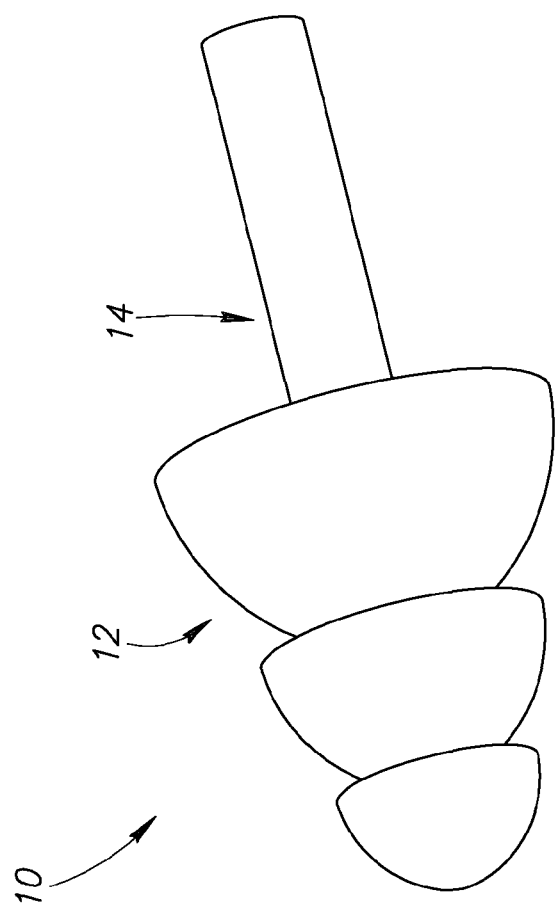
FIG.2
FIG.1

THREE-DIMENSIONAL ATTACHMENT APPARATUS FOR HEARING PROTECTION DEVICES

CROSS-REFERENCE

The current application claims priority to U.S. Provisional Application No. 62/153,413, filed Apr. 27, 2015, the entirety of which is hereby incorporated by reference.

FIELD OF INVENTION

The present invention relates to apparatuses for attachment to hearing protection devices.

BACKGROUND

Wearing hearing protection devices may help to protect against hearing loss due to loud environments, such as those encountered at sporting events or concerts. However, some people may decide not to wear hearing protection devices in loud environments because they perceive that hearing protection devices are unfashionable. Conventional hearing protection devices, such as those shown in FIG. 1, are also not customizable and do not allow a person to show support for their favorite team or band. Ornamental devices do not exist that are attachable to hearing protection devices. Additionally, conventional hearing protection devices are not equipped with peripheral devices.

BRIEF DESCRIPTION OF THE DRAWINGS

FIG. 1 illustrates a side view of a conventional hearing protection device.

FIG. 2 illustrates a side perspective view of an ornamental attachment apparatus according to a first embodiment.

DETAILED DESCRIPTION

Figure 3:
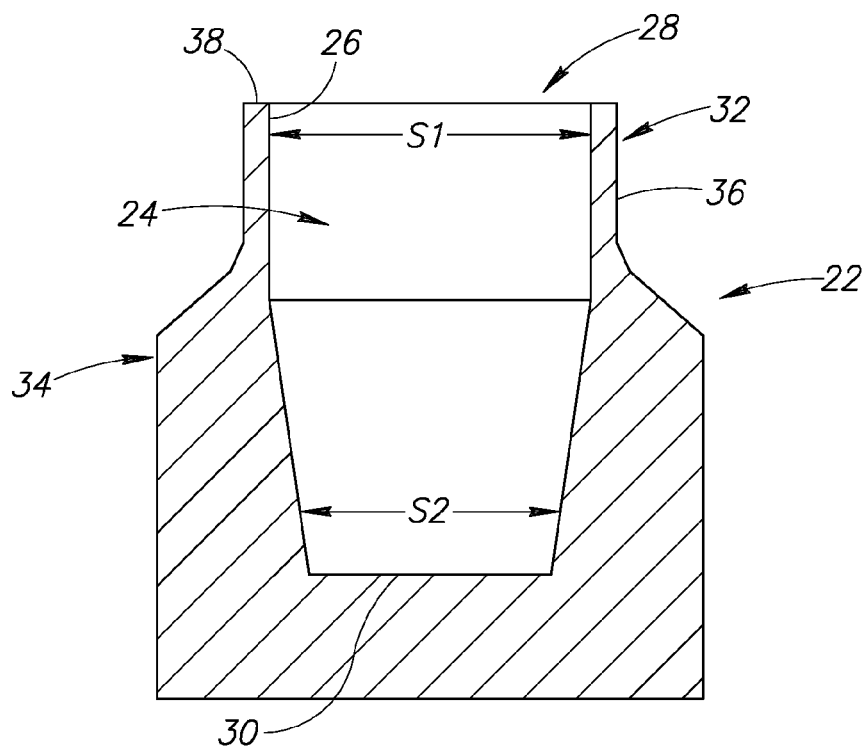
FIG. 3 illustrates a cross-sectional side view of a receiving portion of the ornamental attachment apparatus of FIG. 2.

A reusable hearing protection device 10 of a first type is shown in FIG. 1. The hearing protection device 10 typically includes a hearing protection portion 12 sized and shaped to fit into an ear canal and a post portion 14 having an elongated cylindrical body to facilitate a user to position the hearing protection portion within the ear canal. The reusable hearing protection device 10 is typically comprised of a deformable, resilient material, such as silicone rubber.

An ornamental attachment apparatus 16 according to a first embodiment is shown in FIG. 2. The ornamental attachment apparatus 16 is configured to removably attach to the hearing protection device 10. The ornamental attachment apparatus 16 includes an ornamental portion 18 that has an exterior ornamental feature 20 facing in a first direction. The ornamental feature 20 is a decorative portion that may have a transparent or a semi-transparent portion for allowing illumination by light-emitting devices provided within the ornamental portion 18, as described below. The ornamental feature 20 may have an image thereon (e.g., team logo, band logo), and may have a textured or sculpted surface. The ornamental feature 20 may be removable from and attachable to the ornamental portion 18 to allow the user to customize the ornamental portion.

The ornamental portion 18 allows a wearer of the hearing protection device 10 to decorate the hearing protection device 10 and/or to provide the hearing protection device with a peripheral device. A receiving portion 22 is included on a side of the ornamental attachment apparatus 16 opposite to the ornamental feature 20. The receiving portion 22 has a cavity 24 sized and shaped to receive the post portion 14 of the hearing protection device 10. The cavity 24 opens in a second direction opposite to the first direction. The ornamental portion 18 may have a larger width than the width of the receiving portion 22. A base portion 19 may support the ornamental feature 20, and may have a surface 21 facing in the second direction on a side of the ornamental portion 18 opposite to the ornamental feature. The surface 21 has a substantially flat, slightly convex or slightly concave shape to allow the ornamental attachment apparatus 16 to be closely positioned to the ear when attached to the hearing protection device.

Figure 4:
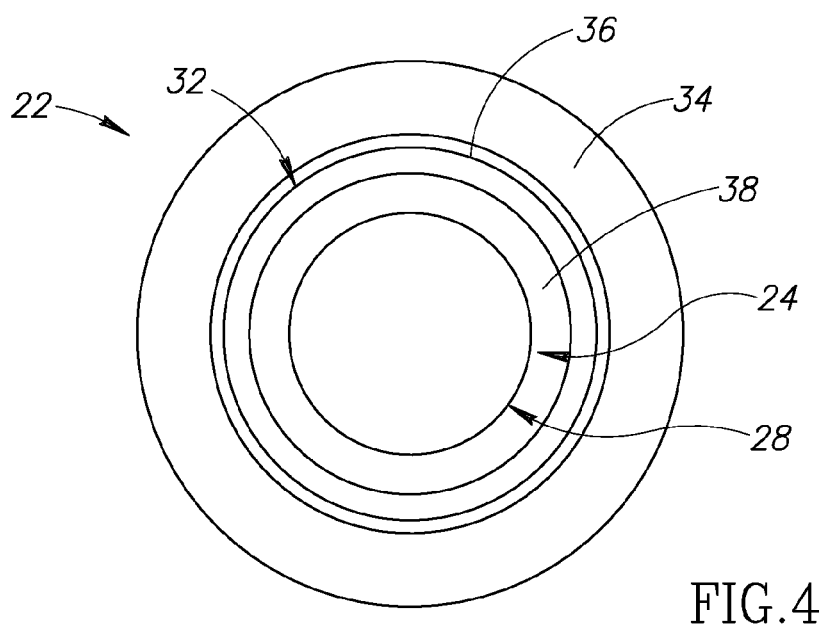
FIG. 4 illustrates a top view of the receiving portion of FIG. 3.

The cavity 24 has a sidewall 26 extending in the second direction from a cavity terminus or cavity end portion 30 toward a cavity aperture 28, as shown in FIG. 3. The cavity aperture 28 of the present embodiment has a round or circular shape, as shown in FIG. 4, corresponding to the cylindrical shape of the post portion 14 of the hearing protection device 10. The cavity aperture 28 may have a diameter equal to or smaller than a diameter of the post portion 14. In embodiments where the cavity aperture 28 is smaller than the diameter of the post portion 14, the post portion may be compressed for insertion into the cavity 24. After insertion into the cavity aperture 28, the post portion 14 may resiliently reform and outwardly press against the sidewall 26. The sidewall 26 may have a textured or high-friction surface to help retain the post portion 14 when inserted into the cavity 24. In some embodiments, the sidewall 26 may have a tapered shape tapering or narrowing away from the cavity aperture 28 such that a first diameter or size S1 at the cavity aperture is larger than a second diameter or size S2 at a point within the cavity 24.

Figure 5:
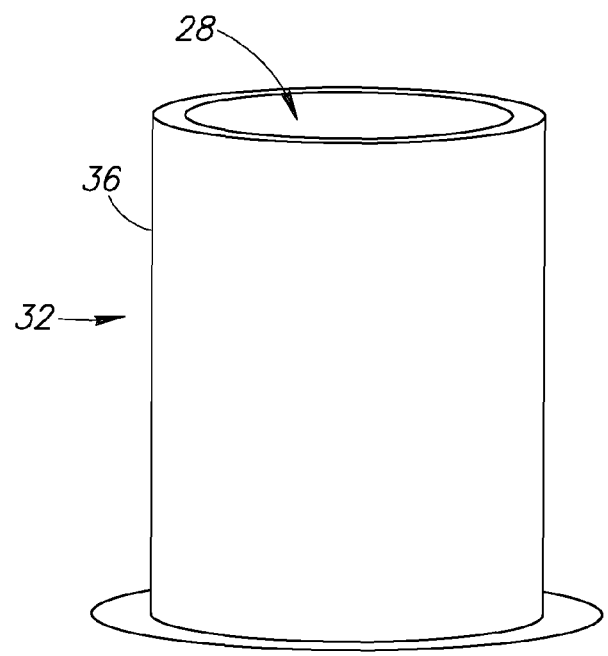
FIG. 5 illustrates a main receiving portion of the receiving portion of FIG. 3.

The receiving portion 22 may include a main receiving portion 32 positioned at least partially within a base portion 34. The main receiving portion 32 may have a cylindrical shape, as shown in FIG. 5. The base portion 34 may provide additional structural support for the main receiving portion 32 or provide a connection between the main receiving portion and the ornamental portion 18. The main receiving portion 32 may include a second sidewall 36 defining an outer side opposite to the sidewall 26. An inner portion 38 between the sidewall 26 and the second sidewall 36 may be hollow or filled with a material. The sidewall 26 may be a different material than the second sidewall 36 in some embodiments. In other embodiments, the sidewall 26, the second sidewall 36 and the inner portion 38 may comprise a monolithic portion formed of the same material.

Figure 6:
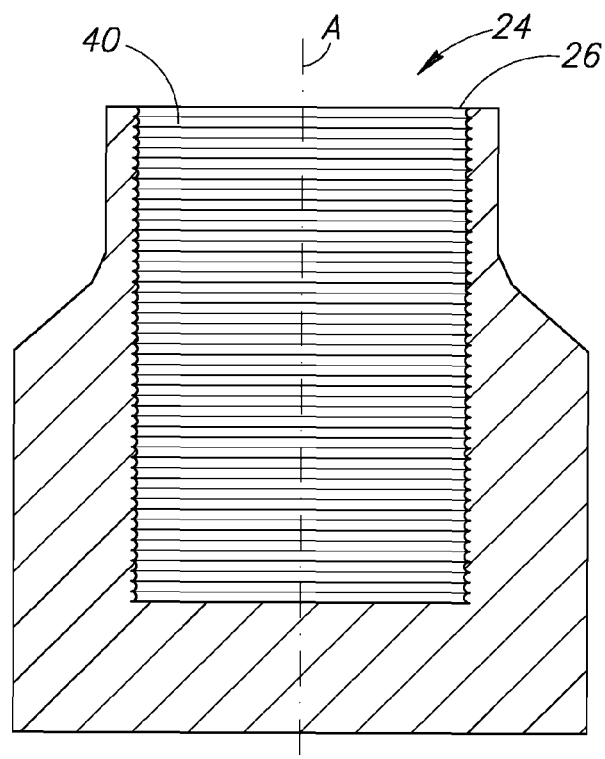
FIG. 6 illustrates a cross-sectional side view of a receiving portion of an ornamental attachment apparatus according to a second embodiment.

The receiving portion 22 may be provided with one or more features for removably securing the post portion 14 of the hearing protection device 10 thereto. The receiving portion 22 may include one or more attachment elements for retaining the post portion 14 received in the cavity 24. In a second embodiment shown in FIG. 6, one or more first attachment elements 40 each protrude radially inward from the cavity sidewall 26. The one or more first attachment elements 40 contact an outer surface of the post portion 14 inserted in the cavity 24, thereby providing a relatively high friction connection between the hearing protection device 10 and the ornamental attachment apparatus 16.

Figure 7:
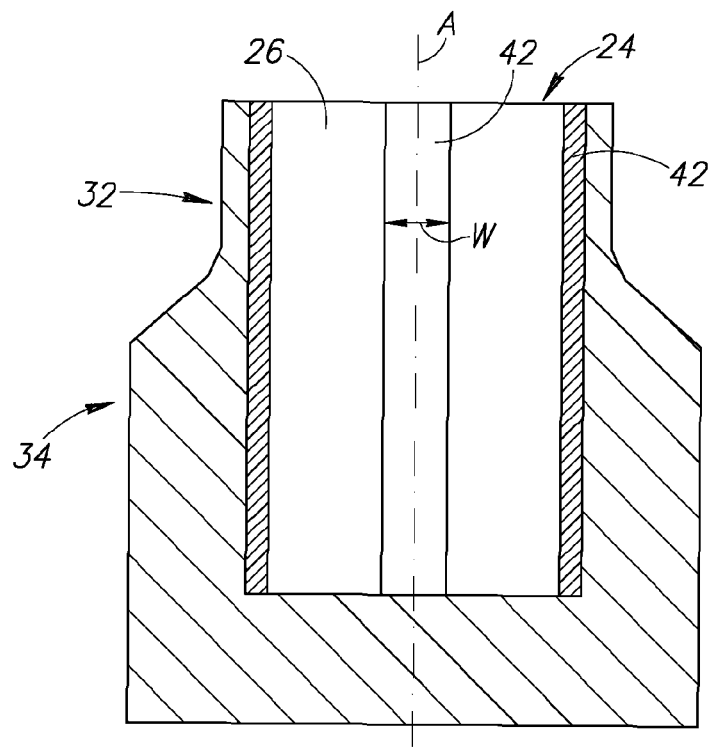
FIG. 7 illustrates a cross-sectional side view of a receiving portion of an ornamental attachment apparatus according to a third embodiment.

The first attachment elements 40 are comprised of a material that has a high coefficient of friction when interfacing with the post portion 14, such as rubber or polymer. The surface of the first attachment elements 40 exposed in the cavity 24 may be coated with an abrasive grit, such as silicone or sand, to increase friction at the interface between the post portion 14 and the first attachment elements. In the present embodiment, the first attachment elements 40 each have an inwardly projecting convex cross-sectional shape. The first attachment elements 40 may have a circular or elliptical cross-sectional shape in some embodiments, or may have a triangular cross-sectional shape with a vertex oriented toward an axial direction A of the cavity 24. Each of the one or more first attachment elements 40 of this second embodiment are annular members that extend along the sidewall 26 in a direction transverse to the axial direction A of the cavity 24. The first attachment elements 40 are positioned adjacent to one another along the axial direction A and may extend in parallel to each other. The first attachment elements 40 of this second embodiment extend in a direction orthogonal to the axial direction A, but may extend at an acute angle with respect to the axial direction. In the present embodiment, the first attachment elements 40 are continuously positioned on the sidewall 26 without an intervening space between adjacent first attachment elements; however, the attachment elements 40 may be spaced apart from each other in the axial direction A in some embodiments. In a third embodiment, the receiving portion 22 includes one or more second attachment elements 42 extending in parallel with the axial direction A of the cavity 24, as shown in FIG. 7. Each of the one or more second attachment elements 42 protrude radially inward from the cavity sidewall 26. Each of the second attachment elements may have a width W extending along an inner periphery of the cavity sidewall 26. The one or more second attachment elements 42 may have a similar shape to, and may be comprised of a similar material to, the one or more first attachment elements 40, so, further description thereof is omitted.

Figure 8:
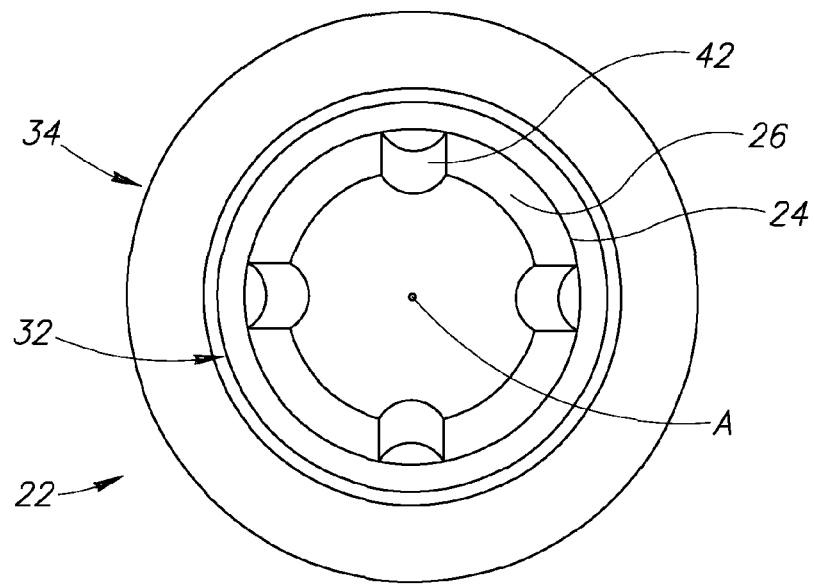
FIG. 8 illustrates a top view of the receiving portion of FIG. 7.

The one or more second attachment elements 42 of this third embodiment are radially positioned along the cavity sidewall 26, as shown in FIG. 8. One of the second attachment elements 42 may oppose another of the second attachment elements that extends along an opposing surface of the cavity sidewall 26. Radially adjacent ones of the second attachment elements 42 are spaced apart along the cavity sidewall 26 in this third embodiment. In some embodiments, however, radially adjacent ones of the second attachment elements 42 may be continuously positioned along the cavity sidewall 26 without a gap therebetween. Each of the second attachment elements 42 may wind around the inner periphery of the cavity sidewall 26 in a helical pattern instead of extending in parallel with the axial direction A1 of the cavity 24.

Figure 9:
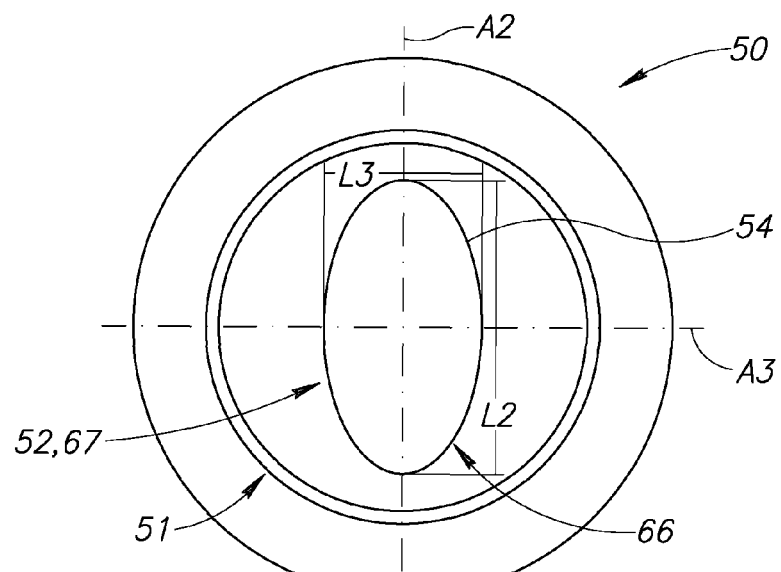
FIG. 9 illustrates a top view of a receiving portion of an ornamental attachment apparatus according to a fourth embodiment.

A third embodiment of an ornamental attachment apparatus 50 is shown in FIG. 9. The ornamental attachment apparatus 50 includes a receiving portion 51 with a cavity 52 having an oblong shape. In particular, a cavity wall 54 of the cavity 52 has an elliptical shape that has a different length along a major axis A2 than a minor axis A3. Specifically, opposing portions of the cavity wall 54 along the major axis A2 are spaced apart at a distance L2 that is longer than a distance L3 between opposing portions of the cavity wall 54 along the minor axis A3. The cavity 52 extends into the receiving portion 51 from a cavity aperture 56 also having the oblong shape.

The cavity walls 54 may extend linearly between the cavity aperture 56 and a cavity terminus at an end of the cavity 52 opposite to the cavity aperture. In some embodiments, the cavity walls 54 may have a tapered shape tapering or narrowing away from the cavity aperture 56 as described above with respect to FIG. 3. The receiving portion 51 may be comprised of a compressible, resilient material, such as silicone rubber, that restores or reforms back to its original shape after being compressed. The distance L2 may be greater than the diameter of the post portion 14 whereas the distance L3 may be less than the diameter of the post portion 14. Radially compressing the receiving portion 51 along the major axis A2 decreases the distance L2 and increases the distance L3 to allow insertion of the post portion 14 within the cavity 52. Once the post portion 14 is inserted within the cavity 52, the receiving portion 51 may be released, which will cause the cavity wall 54 to restore to its original shape (i.e., the distance L2 being longer than the distance L3). The cavity wall 54 along the minor axis A3 will therefore radially compress against the outer cylindrical wall of the post portion 14 to frictionally retain the post portion therein. At least a portion of the cavity wall 54 around the minor axis A3 may be coated with an abrasive grit, such as silicone or sand, to increase the friction at the interface between the post portion 14 and the cavity wall.

Figure 10:
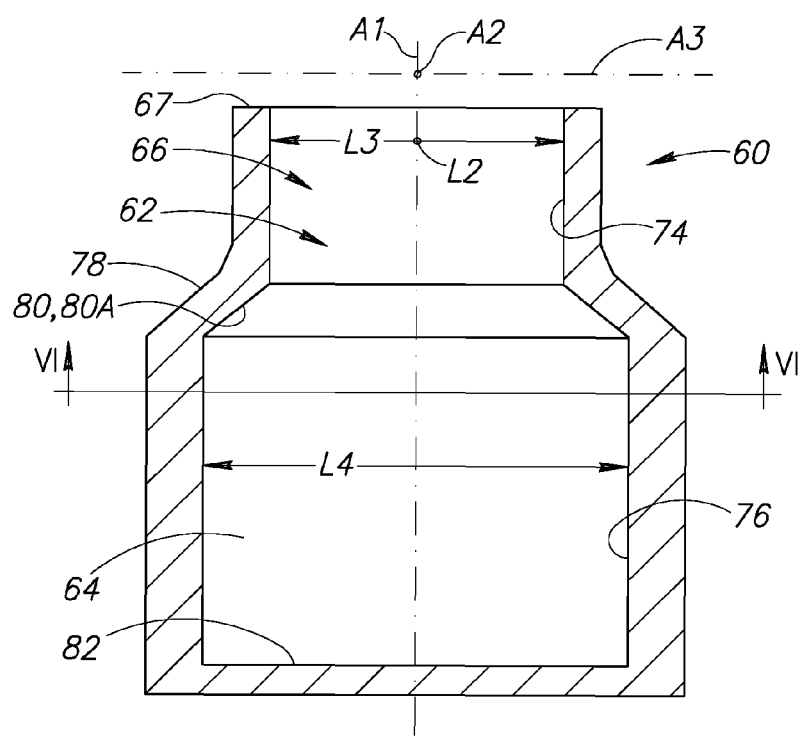
FIG. 10 illustrates a cross-sectional side view of the receiving portion of FIG. 9.
Figure 11:
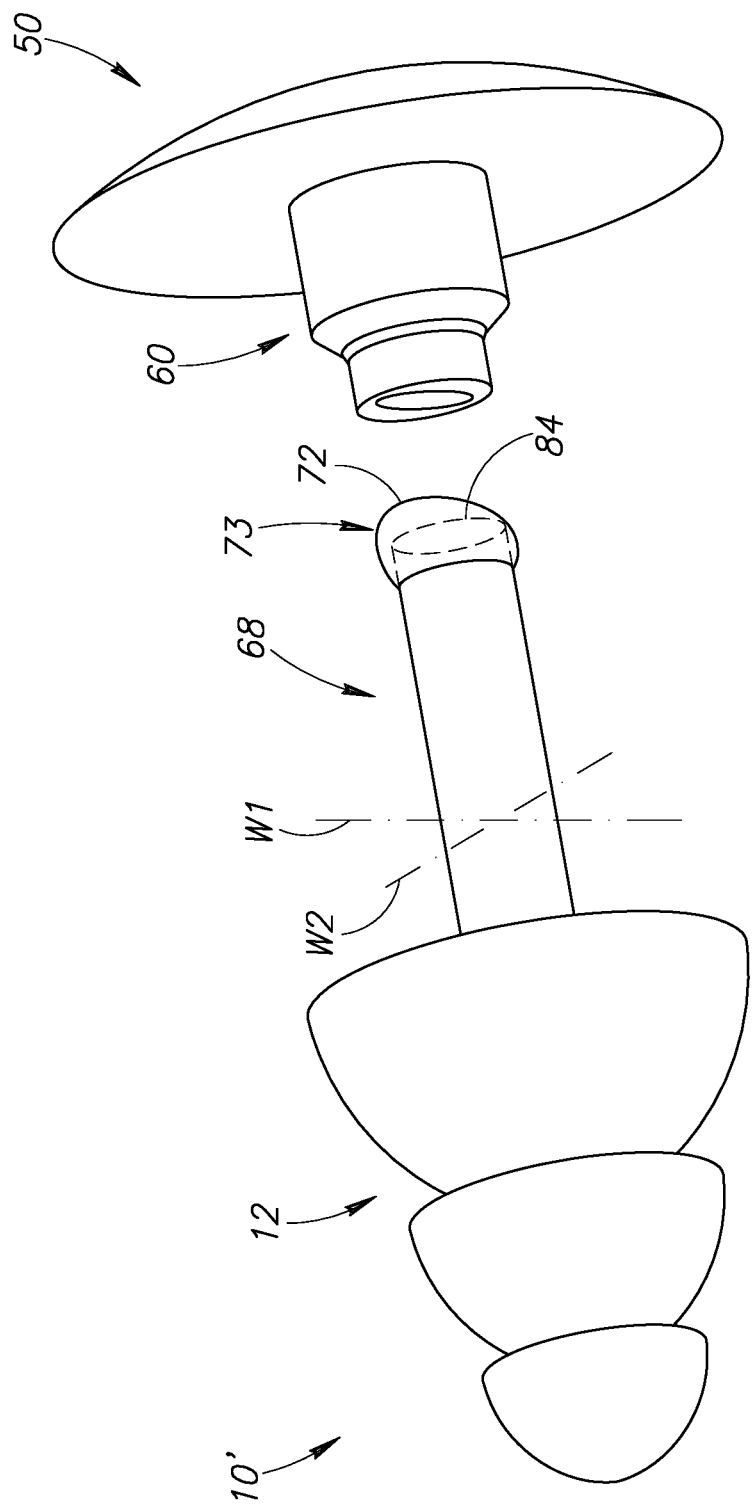
FIG. 11 illustrates a side view of a hearing protection device of a second type.

In a fourth embodiment, a receiving portion 60 of the ornamental attachment apparatus 50 has a cavity 62 including a first cavity portion 64 that is wider than a portion of a second cavity portion 66, as shown in FIG. 10. The receiving portion 60 is sized and shaped to receive a post portion 68 of a hearing protection device 10', the post portion having a first post portion 70 located closer to the hearing protection portion 12 than a second post portion 72. The second post portion 72 has a wide portion 73 that is wider than the first post portion 70 along a first width direction W1, as shown in FIG. 11. The second post portion 72 has a width equal to or less than the first portion along a second width direction W2 orthogonal to the first width direction W1. The first post portion 70 may be a cylindrical portion located closer to the hearing protection portion 12 of the hearing protection device 10'.

Figure 12:
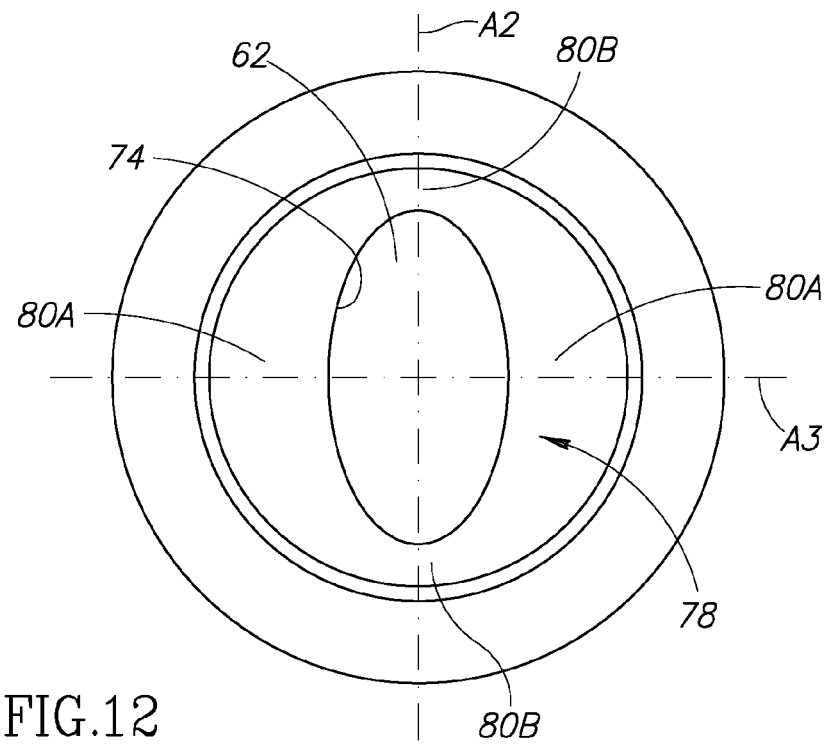
FIG. 12 illustrates a cross-sectional bottom view of the receiving portion of FIG. 9.

The second cavity portion 66 and the cavity aperture 67 have an oblong shape configured to receive the post portion 68 with the second post portion 72 oriented to align with the oblong shape. The oblong shape of the second cavity portion 66 and the cavity aperture 67 may be substantially similar to the oblong shape described with respect to the cavity 52 and the cavity wall 54 shown in FIG. 9. Specifically, the second cavity portion 66 has a distance L2 between opposing portions of a second portion cavity sidewall 74 along a major axis A2 that is greater than a distance L3 between opposing portions of the second portion cavity sidewall along a minor axis A3 orthogonal to the major axis. The first cavity portion 64 has a first portion cavity sidewall 76 having opposing portions spaced apart at a distance L4 greater than the distance L3 between opposing portions of the second portion cavity sidewall 74. A third sidewall portion 78 extends between and connects the first portion cavity sidewall 76 and the second portion cavity sidewall 74. The third sidewall portion 78 has a surface 80 facing downwardly toward a cavity end portion 82. The surface 80 shown in FIG. 10 is oriented at an upwardly projecting acute angle with respect to the minor axis A3; however, the surface 80 may be substantially flat with respect to minor axis A3 in some embodiments. The surface 80 has a first surface portion 80A with a larger surface area below lateral sides of the second cavity portion sidewall 74 along the minor axis A3 than a second surface portion 80B below lateral sides of the second cavity portion along the major axis A2, as best seen in FIG. 12.

Figure 13:
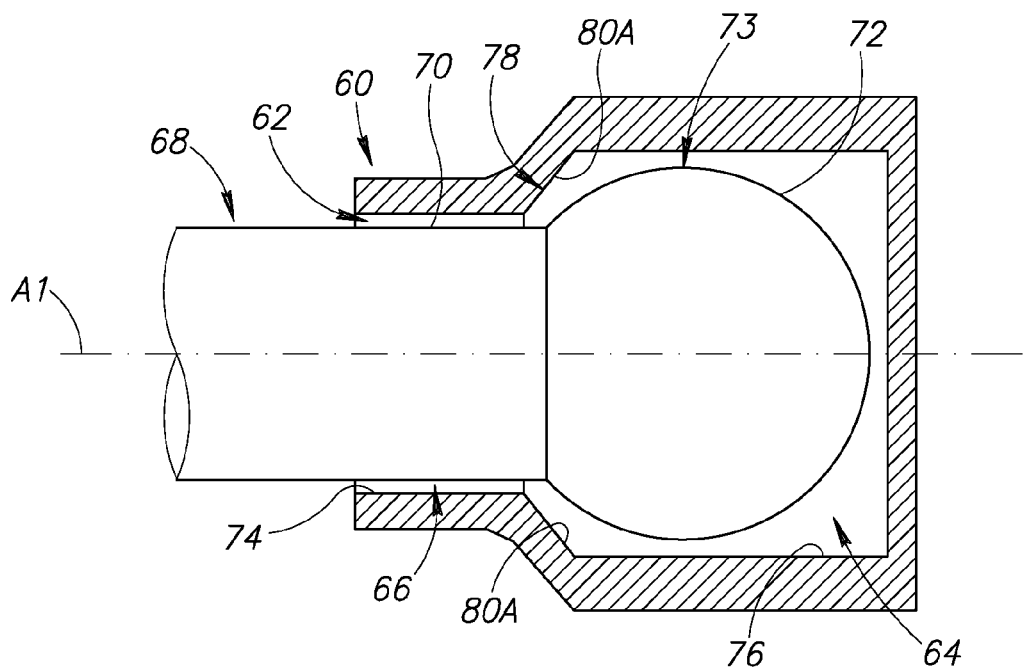
FIG. 13 illustrates a cross-sectional side view of the hearing protection device of FIG. 11 installed in the ornamental attachment apparatus of FIG. 9.

To attach the hearing protection device 10' to the ornamental attachment apparatus 50 having the receiving portion 60, the wide portion 73 of the second post portion 72 is substantially aligned along the major axis A2, then inserted through the first cavity portion 64 and positioned within the second cavity portion 66. Then, the hearing protection device 10' and/or the ornamental attachment apparatus 50 may be relatively rotated about the axial direction A1 to align the wide portion 73 at a retaining position between the first surface portion 80A and the cavity end portion 82, as shown in FIG. 13. When the second post portion 72 is moved away from the cavity end portion 82, the first surface portion 80A abuts an upper side of the wide portion 73 to retain the second post portion 72 within the first cavity portion 64 and thereby selectively attach the hearing protection device 10' to the ornamental attachment apparatus 50. The first cavity portion 64 may include a rotational stop with a surface that abuts a lateral facing side of the wide portion 73 when the second post portion 72 is rotated to the retaining position. Alternatively, the wide portion 73 may be wider than the distance L4 and be comprised of a resilient compressible material that compresses between opposing sides of the first cavity portion sidewall 76 frictionally retaining the wide portion therebetween when the second post portion 72 is rotated to the retaining position.

The second post portion 72 of the post portion 68 may be a separate portion that is securable to the first post portion 70 using an attachment feature. By way of non-limiting example, the second post portion 72 may have a recess 84 sized and shaped to receive an end of the first post portion 70. Adhesives, such as glue, may be used to secure the end of the first post portion 70 within the recess 84. In some embodiments, a fastener or clamp may be used to removably secure the first post portion 70 to the second post portion 72. Alternatively, the hearing protection apparatus 10' may be a monolithically formed unit specially produced for use with the ornamental attachment apparatus 50.

Figure 14:
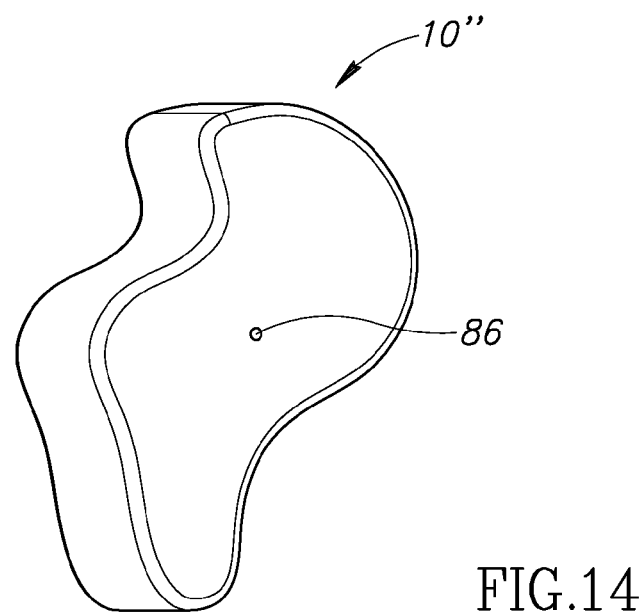
FIG. 14 illustrates a side view of a hearing protection device of the third type.
Figure 15:
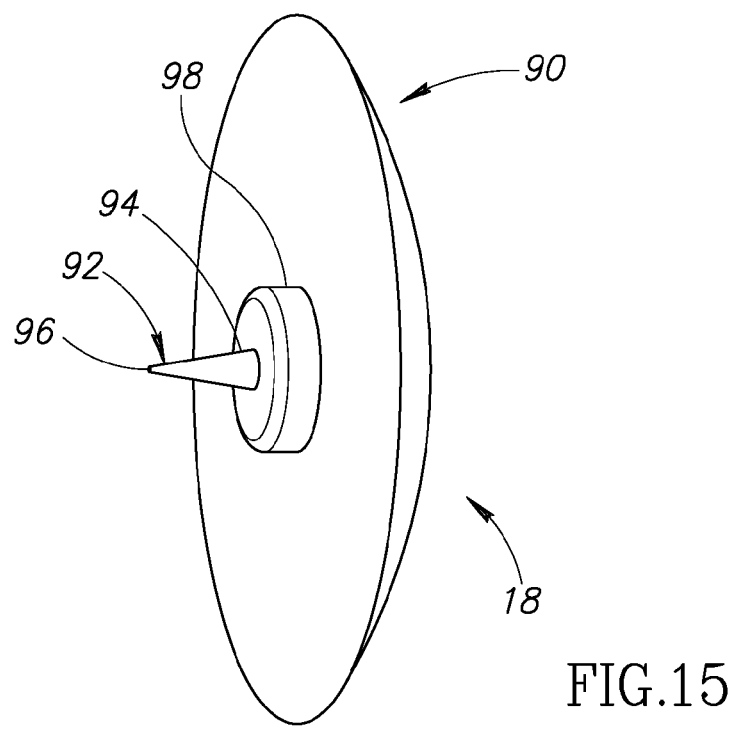
FIG. 15 illustrates an ornamental attachment apparatus according to a fourth embodiment.

A hearing protection device 10" of a second type is shown in FIG. 14. The hearing protection device 10" is comprised of a custom-moldable material that is resilient and compressible, and includes a cavity or attachment portion 86 for receiving a string or cable. An ornamental attachment apparatus 90 according to a fifth embodiment is shown in FIG. 15. The ornamental attachment apparatus 90 has an ornamental portion 18 and an attachment element 92 projecting in an outward direction away from the ornamental portion. The attachment element 92 may have an elongated shape with a first or proximal end 94 closest to the ornamental portion 18 and a second or distal end 96. The attachment element 92 has a tapered shape tapering to a narrowest point at the second end 96. The attachment element 92 of the present embodiment has a circular cross-sectional shape, but may have an elliptical, square or triangular shape in other embodiments. A base portion 98 may connect the ornamental portion to the attachment element 92. The base portion 98 may provide additional structural support for the attachment element 92, or may house electronic components described below.

The attachment element 92 may have one or more features for helping to retain the ornamental attachment apparatus 90 to the hearing protection device 10". The attachment element 92 may have a widest portion that is wider than the cavity 86 of the hearing protection device 10". The widest portion stretches the resilient material surrounding the cavity 86 when the attachment element 92 is inserted therein to help retain the ornamental attachment apparatus 92 the hearing protection device 10". In the present embodiment, the widest portion is the first end 94; however, the widest portion may be a ridge or a disk portion positioned between the first end 94 and the second end 96 along the length of the attachment element 92. The attachment element 92 may be coated with an abrasive grit, such as silicone or sand, to increase the friction between the surface of the attachment element and the surface in the cavity 86.

Figure 16:
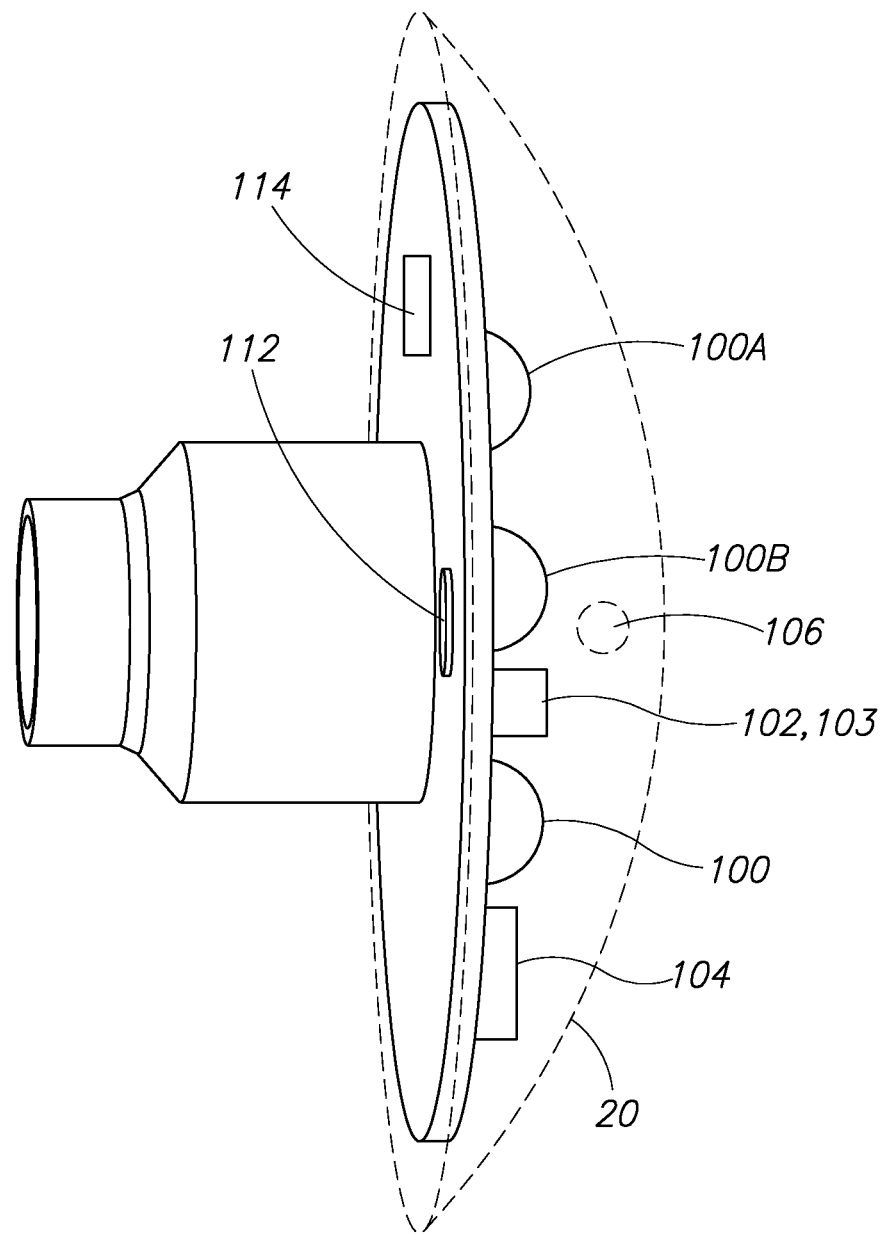
FIG. 16 illustrates a partially transparent view of an ornamental portion of the ornamental attachment apparatus.

The ornamental portion 18 may include one or more peripheral devices adding functionality to the ornamental attachment apparatus. For example, one or more light-emitting devices (LEDs) 100, as shown in FIG. 16, may be disposed on or in the ornamental portion 18 for illuminating the ornamental feature 20. The ornamental feature 20 may include a logo or design with transparent or semitransparent aspects for transmitting light from the one or more LEDs 100 therethrough. The one or more LEDs 100 may be configured to illuminate in response to an environmental stimulus, such as sound, light or vibration. The ornamental portion 18 may include a sensor 102 configured to produce an electronic signal in response to a corresponding environmental stimulus.

An electronic component 104, which may include more than one electronic component (e.g., ICs, op-amps, passive electronic components, microprocessors), may be provided in the ornamental portion 18 operatively connecting the one or more peripheral devices and the sensor 102. The electronic component 104 may include a processing unit for analyzing the electronic signals from the sensor 102 and/or for controlling the one or more peripheral devices. The electronic component 104 may further include signal processing components (e.g., analog-to-digital converters) and/or signal conditioning components (e.g., filters, amplifiers) for processing, converting or conditioning the electronic signal received from the sensor 102. The electronic component(s) 104 may send a control signal to the peripheral device(s) in response to receiving an electronic signal having a predetermined characteristic from the sensor 102.

In the present embodiment, the sensor 102 is a microphone 103 sized to fit on or at least partially within the ornamental portion 18. The ornamental portion 18 may have an aperture 106 extending from an exterior surface to an interior portion where the microphone is located to provide a pathway for receiving sound waves. The electronic component 104 may receive an audio electronic signal from the microphone 103 corresponding to environmental sound around the ornamental attachment apparatus. The electronic component 104 may be configured to analyze the received electronic signal and control an aspect of one or more LEDs 100 in response to results of the analysis.

As a non-limiting example, the electronic component 104 may include hardware or software for analyzing the received audio electronic signal and to control the LED(s) 100 based on one or more audio characteristics of the audio electronic signal, such as volume or frequency. The electronic component 104 may be configured to determine whether the volume (i.e., sound pressure) of the environmental sound equals or exceeds a predetermined volume threshold (e.g., 85 dB). A comparator circuit or comparison function included in the electronic component(s) 104 may compare the received audio signal with a reference signal or a reference level corresponding to the predetermined volume threshold. When the amplitude of the received audio signal equals or exceeds the amplitude of the reference signal or the reference level, the electronic component(s) 104 send a control signal controlling an illumination characteristic of one or more of the LEDs 100. The illumination characteristic may be a brightness of the LEDs 100, such as causing one or more of the LEDs to illuminate, to increase in brightness, or to decrease in brightness. Controlling the illumination characteristics of the one or more LEDs 100 responsive to sound amplitude may warn surrounding persons that they should wear hearing protection because the volume of the environmental sound is sufficient to cause hearing loss.

The electronic component 104 may control other illumination aspects of the LEDs 100, such as an illumination pattern or illumination color. The illumination pattern may be a pattern of successive LED illumination periods. When more than one LED 100 is provided on or in the ornamental portion 18, the illumination pattern may include illuminating ones of the LEDs at different times. The LEDs 100 may comprise LEDs of different colors in some embodiments. The electronic component 104 may illuminate LEDs of different colors according to different audio characteristics. For example, the electronic component 104 may control the illumination characteristics of LEDs 100A having a first color when the sound volume is within a first range (e.g., illuminate green LED between 0-60 dB), and may control the illumination characteristic of LEDs 100B having a second color when the sound volume is within a second range (e.g., illuminate red LED when equal to or greater than 85 dB).

The sensor 102 may detect or measure environmental characteristics other than sound. In some embodiments, the sensor 102 may be an optical sensor configured to detect luminance or frequency (i.e., color) of surrounding light. The electronic component 104 may be configured to illuminate one or more of the LEDs based on the presence of surrounding light, or based on the color of the surrounding light. In other embodiments, the sensor 102 may be an accelerometer configured to measure vibration. The electronic component 104 may be configured to illuminate one or more of the LEDs 100 based on detecting a vibration exceeding a predetermined vibrational threshold indicating a user footstep or jump. The ornamental portion 18 may include more than one sensor 102 to facilitate detecting or measuring more than one environmental characteristic.

The ornamental portion 18 may have peripheral devices different than LEDs 100. The peripheral devices may include a wireless communication device 108 that transmits or receives information regarding the sensor 102 and/or another peripheral device. The wireless indication device 108 may be one or more of an RF transceiver, a Wi-Fi transceiver, a Zigbee transceiver, or a Bluetooth transceiver, by way of non-limiting example. The wireless communication device 108 and/or electronic component 104 may be configured to wirelessly communicate information with an application on a mobile device, such as a smartphone or tablet computer. The ornamental portion 18 may further include a storage device 110 (e.g., RAM, ROM) for storing information regarding measurements from the sensor 102 and/or data for controlling at least one peripheral device. The storage device 110 may be electronically connected to one or more of the sensor 102, the peripheral device (e.g., LED 100), and or the electronic component 104.

In one application, the electronic component 104 may generate and transmit sensor information regarding the electronic signal received from the sensor 102 to the wireless communication device 108. The sensor information of the current embodiment may include waveform, amplitude and frequency information related to the audio environment surrounding the ornamental attachment apparatus 18. The wireless communication device 108 may transmit the sensor information to a nearby electronic communication device, such as a Wi-Fi router or a mobile device, for storage, processing or analysis. Transmitting the sensor information from the wireless communication device 108 to the nearby electronic communication device may allow a user to review the collected sensor data for analysis regarding the environment. For example, the user could review audio data regarding the crowd noise at an event, such as a football game, attended by the user. In another aspect, real-time data could be collected and aggregated from different ornamental attachment devices during an event to allow different sections in a sporting venue to compete with each other for loudest section.

In another application, the wireless communication device 108 may receive control or programming data for controlling the LEDs 100 or another peripheral device. The control or programming data may be stored on the storage device 110 and executed by the electronic component 104. Alternatively, the control or programming data may be stored on or executed by firmware associated with the LEDs 100 or peripheral device. Execution of the control or programming data causes the electronic component 104 to illuminate the LEDs 100 according to an illumination pattern (e.g., illumination intervals, color scheme, predetermined illumination timing). The control or programming data may allow additional control of the peripheral devices, including adjusting the predetermined threshold for controlling illumination aspects of the LEDs 100.

Figure 17:
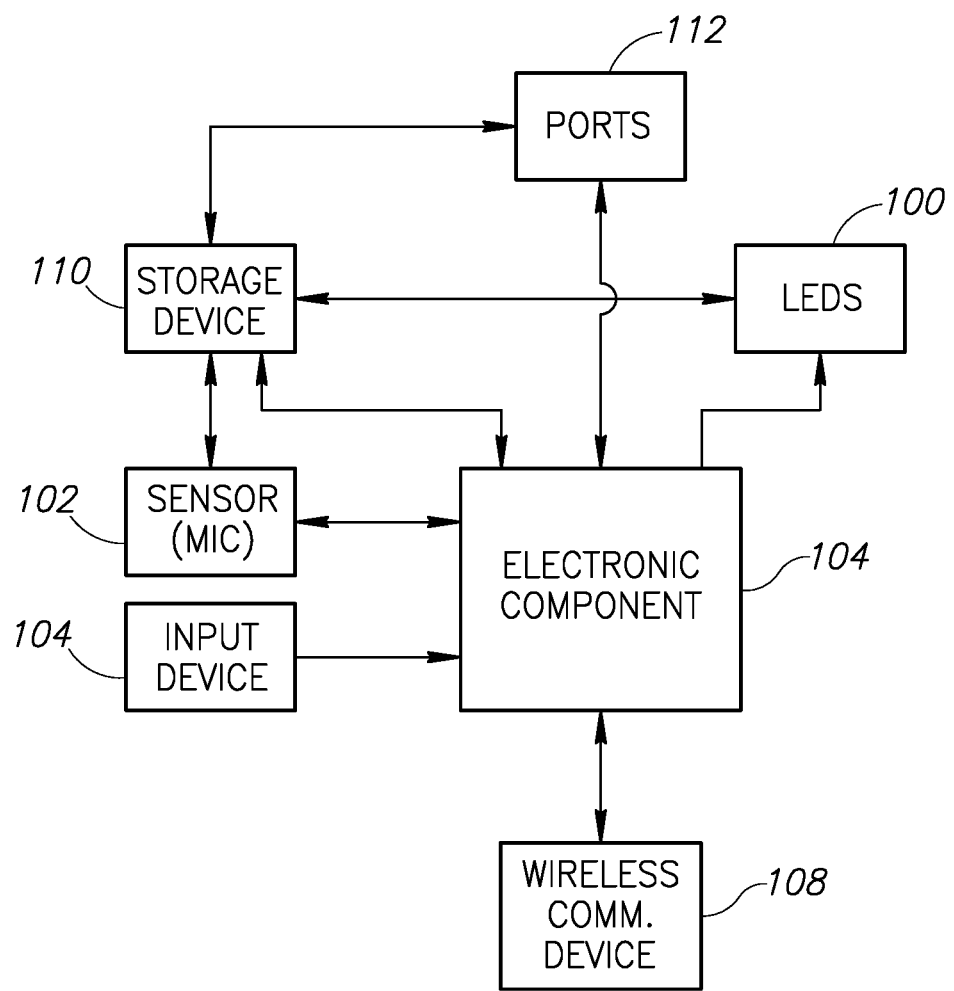
FIG. 17 illustrates a schematic view of components of the ornamental portion of FIG. 16.

The ornamental portion 18 may include other features for increasing user interaction therewith. A port 112 may be provided on the ornamental portion 18, as best seen in FIG. 16, for charging an internal battery therein, or for transmitting and receiving the sensor information or the control or programming data described above. The port 112 may be a micro-USB port electronically coupled to the internal battery, the electronic component 104 and/or the storage device 110, as shown in FIG. 17. A user input feature 114, such as a button or a switch, may be provided on a surface of the ornamental portion 18 for allowing manual user control of the peripheral devices. For example, interacting with the user input feature 114 (e.g., pressing the button) may manually illuminate the LED(s) 100 or may transition the peripheral devices and/or electronic component between an on state and an off state.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Accordingly, the invention is not limited except as by the appended claims.

What is claimed is:

1. An ornamental attachment apparatus for attaching to a hearing protection device having a sound attenuation portion for removable insertion into an ear canal and a cylindrical post portion for enabling user removal and insertion of the sound attenuation portion into the ear canal, the attachment apparatus comprising:
    an ornamental portion having an ornamental feature facing in a first direction and a base portion supporting the ornamental feature; and
    a receiving portion including a cavity extending in a second direction opposite to the first direction on or in the base portion and including an attachment element positioned within the cavity, the cavity being sized and shaped to receive a post portion of the hearing protection device, the attachment element being configured to frictionally secure the post portion in the cavity.

2. The ornamental attachment apparatus of claim 1, wherein the base portion has a base surface facing in the second direction, and the cavity is defined by cavity walls extending from the base surface.

3. The ornamental attachment apparatus of claim 1, wherein the attachment element is a protruding portion protruding radially inward from a cavity wall extending in the second direction and defining the cavity.

4. The ornamental attachment apparatus of claim 3, wherein the protruding portion extends linearly along the cavity wall.

5. The ornamental attachment apparatus of claim 3, wherein the protruding portion extends in parallel to the second direction along the cavity wall.

6. The ornamental attachment apparatus of claim 3, wherein the protruding portion extends in a circumferential direction along the cavity wall.

7. The ornamental attachment apparatus of claim 3, wherein the protruding portion is convex ridge portion extending along an inner surface of the cavity wall.

8. The ornamental attachment apparatus of claim 1, wherein the receiving portion includes a plurality of attachment elements, two more of thea attachment elements being protruding portions protruding radially inward from a cavity wall.

9. The ornamental attachment apparatus of claim 8, wherein adjacent ones of the attachment elements extend in parallel with each other along the cavity wall.

10. The ornamental attachment apparatus of claim 9, wherein the adjacent ones of the attachment elements are spaced apart from each other along the cavity wall.

11. The ornamental attachment apparatus of claim 9, wherein the adjacent ones of the attachment elements are immediately positioned next to each other along the cavity wall without space therebetween.

12. The ornamental attachment apparatus of claim 8, wherein the plurality attachment elements extend in the second direction along the cavity wall.

13. The ornamental attachment apparatus of claim 8, wherein the plurality attachment elements extend in a circumferential direction along the cavity wall.

14. The ornamental attachment apparatus of claim 1, wherein the receiving portion projects outwardly in the second direction from the ornamental portion.

15. The ornamental attachment apparatus of claim 14, wherein the receiving portion has a cylindrical shape.

16. The ornamental attachment apparatus of claim 1, wherein the cavity has a round cross-sectional shape.

17. The ornamental attachment apparatus of claim 1, wherein the ornamental portion includes a sensor configured to produce an electronic signal in response to an environmental stimulus, a light-emitting device and an electronic component electronically coupled to the sensor and the light-emitting device, the electronic component configured to control the light-emitting device responsive to receiving the electronic signal from the sensor.

18. An ornamental attachment apparatus for attaching to a hearing protection device having a sound attenuation portion for removable insertion into an ear canal and a cylindrical post portion for enabling user removal and insertion of the sound attenuation portion into the ear canal, the attachment apparatus comprising:
    an ornamental portion having an externally facing ornamental feature and a base portion supporting the ornamental feature; and a receiving portion including a cavity defined by cavity walls extending in an axial direction away from the ornamental feature and including a retaining portion having an inner wall with an oblong cross-sectional shape at least partially surrounding the cavity, the receiving portion being compressible to allow insertion of the post portion into the cavity, release of the receiving portion when compressed is operable to frictionally retain the post portion positioned within the cavity.

19. The ornamental attachment apparatus of claim 18, wherein the inner wall extends along a length of the cavity.

20. The ornamental attachment apparatus of claim 18, wherein the receiving portion further comprises a first receiving portion having a first inner wall portion with a second oblong cross-sectional shape surrounding a first cavity portion, and a second receiving portion having a round shape surrounding a second cavity portion that is closer to the ornamental portion than the first cavity portion, the retaining portion being positioned between the first receiving portion and the second receiving portion.

21. The ornamental attachment apparatus of claim 20, wherein a length direction of the inner wall is oriented in a first orientation about the axial direction of the cavity, and a length direction of the second oblong cross-sectional shape of the first inner wall portion is oriented in a second orientation about the axial direction different than the first orientation.

22. The ornamental attachment apparatus of claim 18, wherein the inner wall of the retaining portion is oriented at an acute angle with respect to the axial direction.

23. The ornamental attachment apparatus of claim 18, wherein the inner wall faces an end portion of the cavity closest to the ornamental portion.

24. The ornamental attachment apparatus of claim 18, wherein the ornamental portion includes a sensor configured to produce an electronic signal in response to an environmental stimulus, a light-emitting device and an electronic component electronically coupled to the sensor and the light-emitting device, the electronic component configured to control the light-emitting device responsive to the electronic signal received from the sensor.

25. An ornamental attachment apparatus for attaching to a hearing protection device having a sound attenuation portion for removable insertion into an ear canal and a cylindrical post portion for enabling user removal and insertion of the sound attenuation portion into the ear canal, the attachment apparatus comprising:
an ornamental portion having an ornamental feature;
a peripheral device disposed in the ornamental portion;
a receiving portion coupled to the ornamental portion and configured to attach the hearing protection device to the ornamental portion by at least frictionally securing the post portion positioned within a cavity of the receiving portion;
a sensor device configured to produce an electronic signal responsive to an environmental stimulus; and
an electronic component electrically coupled to the sensor and the peripheral device and configured to control the peripheral device responsive to receiving the electronic signal from the sensor device.

26. The ornamental attachment apparatus of claim 25, wherein the electronic component is housed in the ornamental portion.

27. The ornamental attachment apparatus of claim 25, wherein the peripheral device is a light-emitting device, and the sensor device is a microphone.

28. The ornamental attachment apparatus of claim 25, wherein the electronic component is configured to control a characteristic of the peripheral device in response to a determination that the electronic signal received from the sensor device exceeds a predetermined threshold.

29. The ornamental attachment apparatus of claim 28, wherein the illumination characteristic is a brightness of the light-emitting device, and the predetermined threshold is a predetermined amplitude threshold.

30. The ornamental attachment apparatus of claim 28, wherein the illumination characteristic is an emission color of the light-emitting device.

31. The ornamental attachment apparatus of claim 25, wherein the peripheral device is a wireless communication device, and the sensor device is a microphone.

32. The ornamental attachment apparatus of claim 31, wherein the electronic component is configured to process the electronic signal received from the microphone, and the wireless communication device is configured to transmit a wireless signal containing information regarding the electronic signal received from the microphone.

33. The ornamental attachment apparatus of claim 31, wherein the ornamental attachment apparatus further comprises a second peripheral device.

34. The ornamental attachment apparatus of claim 33, wherein the second peripheral device is a light-emitting device, the wireless communication device is configured to receive a wireless control signal, and the electronic component is configured to control an illumination aspect of the light-emitting device in response to control information contained in the wireless control signal.

* * * * *